(12) United States Patent
Talin et al.

(10) Patent No.: US 9,546,887 B1
(45) Date of Patent: Jan. 17, 2017

(54) MULTIAXIS SENSING USING METAL ORGANIC FRAMEWORKS

(71) Applicant: Sandia Corporation, Albuquerque, NM (US)

(72) Inventors: Albert Alec Talin, Dublin, CA (US); Mark D. Allendorf, Pleasanton, CA (US); Francois Leonard, Brentwood, CA (US); Vitalie Stavila, Pleasanton, CA (US)

(73) Assignee: Sandia Corporation, Albuquerque, NM (US)

( * ) Notice: Subject to any disclaimer, the term of this patent is extended or adjusted under 35 U.S.C. 154(b) by 167 days.

(21) Appl. No.: 14/573,990

(22) Filed: Dec. 17, 2014

Related U.S. Application Data

(60) Provisional application No. 61/918,384, filed on Dec. 19, 2013.

(51) Int. Cl.
| | |
|---|---|
| *G01N 27/00* | (2006.01) |
| *G01N 33/00* | (2006.01) |
| *G01N 27/10* | (2006.01) |
| *G01D 5/54* | (2006.01) |
| *G01N 27/12* | (2006.01) |
| *B01J 20/22* | (2006.01) |
| *C40B 60/12* | (2006.01) |
| *G01N 30/96* | (2006.01) |
| *G01N 29/02* | (2006.01) |

(52) U.S. Cl.
CPC .............. *G01D 5/54* (2013.01); *B01J 20/226* (2013.01); *G01N 27/125* (2013.01); *B01D 2253/204* (2013.01); *G01N 29/022* (2013.01); *G01N 33/004* (2013.01); *G01N 33/0027* (2013.01); *G01N 2291/02809* (2013.01)

(58) Field of Classification Search
CPC .............. B01J 20/226; G01N 29/022; G01N 2291/02809; G01N 33/0027; B01D 2253/204
See application file for complete search history.

(56) References Cited

U.S. PATENT DOCUMENTS

| | | | |
|---|---|---|---|
| 5,763,283 A | 6/1998 | Cernosek et al. | |
| 7,908,902 B2 * | 3/2011 | Levitsky | G01N 1/2205 73/31.07 |
| 8,065,904 B1 * | 11/2011 | Allendorf | G01N 29/022 73/23.2 |

(Continued)

OTHER PUBLICATIONS

Allendorf, et al., "Stress-induced chemical detection using flexible metal-organic frameworks," J Am Chem Soc., Nov. 5, 2008; 130(44):14404-5.

(Continued)

*Primary Examiner* — Jennifer Wecker
(74) *Attorney, Agent, or Firm* — Blakely, Sokoloff, Taylor & Zafman, LLP

(57) ABSTRACT

A sensor device including a sensor substrate; and a thin film comprising a porous metal organic framework (MOF) on the substrate that presents more than one transduction mechanism when exposed to an analyte. A method including exposing a porous metal organic framework (MOF) on a substrate to an analyte; and identifying more than one transduction mechanism in response to the exposure to the analyte.

18 Claims, 4 Drawing Sheets

(56) References Cited

U.S. PATENT DOCUMENTS

| | | | |
|---|---|---|---|
| 2009/0203000 A1* | 8/2009 | Mutharasan | G01N 33/54373 435/6.12 |
| 2012/0028846 A1* | 2/2012 | Yaghi | G01N 27/125 506/39 |
| 2012/0282142 A1* | 11/2012 | Fleischer | G01N 27/4143 422/98 |
| 2014/0011286 A1* | 1/2014 | Potyrailo | G01N 33/0031 436/149 |
| 2015/0020577 A1* | 1/2015 | Luebke | G01N 27/12 73/31.06 |

OTHER PUBLICATIONS

Potyrailo, et al., "Materials and transducers toward selective wireless gas sensing," Chem Rev. No. 9, 2011; 111(11):7315-7354.
Robinson, et al., "Ultrasensitive humidity detection using metal-organic framework-coated microsensors," Anal Chem., Aug. 21, 2012; 84(16):7043-51.

* cited by examiner

MULTIAXIS SENSING USING METAL ORGANIC FRAMEWORKS

CROSS-REFERENCE TO RELATED APPLICATION

This application claims the benefit of the earlier filing date of U.S. Provisional Patent Application No. 61/918,384, filed Dec. 19, 2013 entitled "Multiaxis Sensing Using Electrically Conducting MOFs." The aforementioned application is hereby incorporated by reference, in its entirety, for all purposes.

STATEMENT OF GOVERNMENT RIGHTS

This invention was developed under Contract DE-AC04-94AL85000 between Sandia Corporation and the U.S. Department of Energy. The U.S. Government has certain rights in this invention.

FIELD

Analyte sensors.

BACKGROUND

It is generally difficult to identify an analyte in a multi-component background with high concentrations of interfering species without high false positives. Sensor arrays and separation techniques can address this problem, but add considerable cost and complexity. A reason for this lack of selectivity is in part due to the fact that most materials can detect a given analyte only by a single transduction mechanism (i.e., a way of translating the "event" in which the analyte encounters the sensor into a recognizable signal of some kind—electrical, optical, acoustic, etc.)

SUMMARY

A sensor device including a sensor substrate; and a thin film comprising a porous metal organic framework (MOF) on the substrate that presents more than one transduction mechanism when exposed to an analyte. A method including exposing a porous metal organic framework (MOF) on a substrate to an analyte; and identifying more than one transduction mechanism in response to the exposure to the analyte.

BRIEF DESCRIPTION OF THE DRAWINGS

The invention may best be understood by referring to the following description and accompanying drawings that are used to illustrate embodiments of the invention. In the drawings.

DETAILED DESCRIPTION

Figure 1:
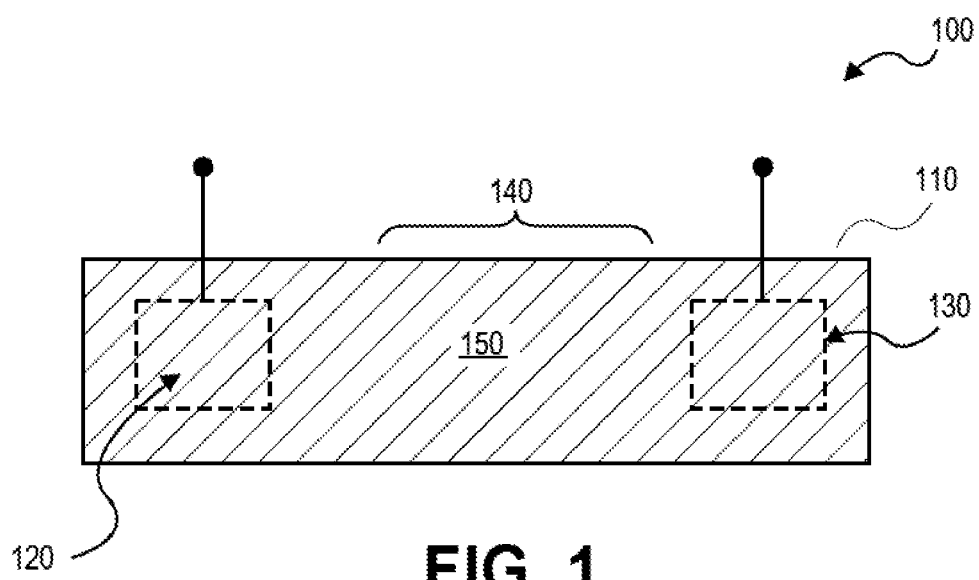
FIG. 1 shows a top view of an embodiment of a surface acoustic wave sensor device including a MOF film.

In one embodiment, a device is described that includes a sensor substrate and a thin film comprising a porous metal organic framework (MOF) that presents more than one transduction mechanism when exposed to an analyte. Materials that modify more than one transduction mechanism in response to interaction with an analyte enable "multi-axis" sensing. Thus, in another embodiment, a method is described that includes exposing a MOF to an analyte. An example of transduction mechanisms associated with a MOF's exposure to an analyte is a MOF could change color and its electrical resistance when a molecule binds to the material. Since these transduction mechanisms have their origin in entirely different physical processes, the changes in two or more different properties will not have the same functional behavior, i.e., they are mathematically independent of each other. This enables a "fingerprint" to be identified for a given analyte that will be different from that of other analytes, thereby enabling selective analyte detection.

MOFs are crystalline, nanoporous materials composed of metal ions linked by rigid organic ligands. Their surface areas, tailorable pore size, and tunable pore environment make them attractive as chemical recognition layers for sensing purposes.

In one embodiment, a MOF is a compound including metal ions or clusters coordinated to organic ligands. Suitable metal ions or clusters include copper ions (e.g., $Cu^{2+}$), and ions of chromium (Cr), iron (Fe), nickel (Ni), molybdenum (Mo) and ruthenium (Ru). In one embodiment, a suitable MOF includes $Cu_3(BTC)_2$ also known as HKUST-1.

In one embodiment, the MOF itself is the material that presents more than one transduction mechanism when exposed to an analyte, either by changing a property or effecting a change (e.g., effecting a change of another material to which the MOF is connected). In another embodiment, the MOF includes a guest species that modifies the MOF and it is the modified MOF (MOF plus guest species) that presents more than one transduction mechanism when exposed to an analyte. A representative guest species is a species that participates in charge transfer with the MOF and includes a delocalized p electron or p electrons. Representative guest species include one or more nitrile moieties, one or more thiol moieties, one or more carbonyl moieties, one or more thiolate moieties, one or more amine moieties, one or more imine moieties, one or more hydroxyl moieties, or a mixture thereof. A moiety is used generally to identify a portion of a molecule. In one embodiment, the guest species is 7,7,8,8-tetracyanoquinododimethane (TCNQ), a molecule having multiple nitrile moieties. In one embodiment, a composition includes a porous MOF of $Cu_3(BTC)_2$ and a guest species of TCNQ. Without wishing to be bound by theory, it is believed the recited moieties of respective molecules participate in the charge transfer with the MOF and thus, are responsible for imparting electrical conductivity to the composition (MOF and guest species). In another embodiment, a representative guest species is a molecule that has a configuration that will interact with a MOF to impart electrical conductivity. Representative molecules include thiophenes, dithiophenes, tetrathiafulvalene, imidazole, triazole, tetrazole and derivatives and/or mixtures thereof. In a further embodiment, a representative guest species is a transition metal complex operable to undergo an outer sphere electron transfer. Examples include, but are not limited to, ruthenium hexamine, hexacyanoferrate and hexacyanocobaltrate. Such complexes can be assembled into bulk semiconducting coordination polymers operable to undergo a charge transfer reaction with a MOF resulting in conducting behavior.

A multi-axis sensor can be created using a thin film of an electrically conducting, nanoporous MOF. Such films exhibit properties that, when measured simultaneously, enable detection of a species in contact with the film using multiple transduction mechanisms. An example of a conducting MOF is HKUST-1 infiltrated with the molecule TCNQ. Molecular sensing can occur by measuring a change in electrical conductivity and, for example, interfacial strain.

In one embodiment, a sensor device is a surface acoustic wave (SAW) sensor device. FIG. 1 shows a top view of an embodiment of a SAW device including a MOF film. SAW device 100 includes piezoelectric substrate 110 with input transducer 120 on one side and output transducer 130 on an opposite side. In this embodiment, input transducer 120 and output transducer 130 each include electrodes of, for example, gold or platinum. Delay line or area 140 is an area between the transducers. In one embodiment, a thin film of a MOF or a modified MOF that presents more than one transduction mechanism is disposed (deposited) on delay line 140. In another embodiment, as shown, thin film 150 of a MOF or a modified MOF is disposed on the entire surface of substrate 110 including on each transducer. Representatively, a thin film of a MOF such as $Cu_3(BTC)_2$ may have a thickness on the order of 100 nanometers (nm) to 200 nm that may be grown or deposited on substrate 110 by a technique as described in the art (e.g., grown in a liquid cell reactor). SAW device 110 transduces an input electrical signal into a mechanical wave that can be influenced by physical phenomena. The device then transduces this wave back into an electrical signal. Changes in amplitude, phase, acoustic frequency, or time-delay between the input and output electrical signals represent at least one transduction mechanism that can be detected according to techniques known in the art. Exposing a modified MOF of, for example, HKUST-1 with a guest species of TCNQ to an analyte of water will cause the modified MOF to uptake the water and modify the acoustic frequency of the sensor (a first transduction mechanism). The modified MOF will also change its electrical conductivity in response to exposure to water a second transduction mechanism).

Figure 2:
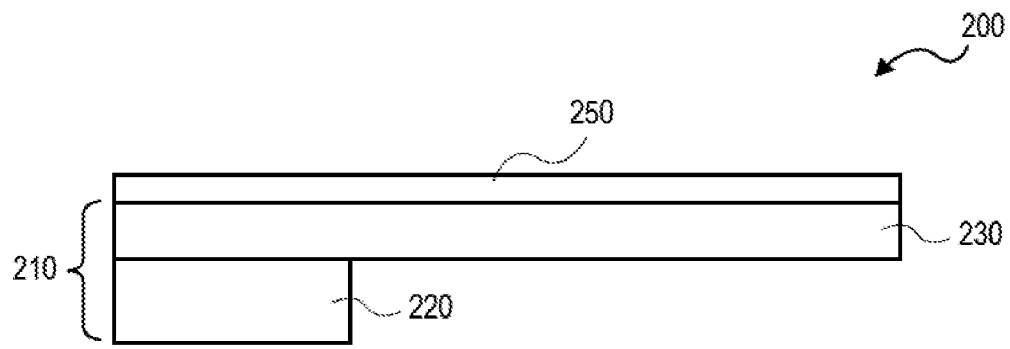
FIG. 2 shows a side view of an embodiment of a microcantilever device including a MOF film.

In another embodiment, a sensor device is a microcantilever sensor device. FIG. 2 shows a side view of an embodiment of a microcantilever device including a MOF film. Device 200 includes microcantilever 210, including base 220 and beam 230. Microcantilever may be formed of a semiconductor material such as silicon or a material such as silicon nitride or a polymer as known in the art of microelectromechanical systems (MEMS). Disposed on a surface (top surface as viewed) of beam 230 is thin film 250 of a MOF or a modified MOF that presents more than one transduction mechanism. Representatively, a thin film of a MOF such as $Cu_3(BTC)_2$ may have a thickness on the order of 100 nm to 200 nm that may be grown or deposited on beam 230. Here, one transduction mechanism is a modification of the strain at the interface between film and the underlying mechanical device (e.g., cantilever 210). In another embodiment, a transduction mechanism is a change in resonance frequency of beam 230 upon exposure to an analyte. Depending on the MOF and the analyte, the strain or resonance frequency may be combined with another transduction mechanism (color, electrical resistance, etc.). To measure electrical conductivity, a two-point method using a standard current/volt meter may be used to measure conductance, one probe contacting each of two MOF-coated contacts of the device, i.e., directly in contact with the film, and the conductivity is deduced by knowing the geometry and thickness of the MOF film.

Sensing combinations of more than one transduction mechanism presented by MOFs on exposure to an analyte include:

1. Electrical conductivity (i.e., measurement of current)+ strain, acoustic modification, or optical absorption/emission.
2. Electrical resistance+strain, acoustic modification, or optical absorption/emission.
3. Electrical impedance+strain, acoustic modification, or optical absorption/emission.
4. Electrical capacitance+strain, acoustic modification, or optical absorption/emission.
5. Electrical resistance+chemical reactions.
6. Electrical resistance+dielectric properties.
7. Electrical resistance+thermal conductivity.
8. Electrical resistance+magnetic properties.
9. Electrical resistance+thermoelectric.

In the above list, changes in optical absorption/emission refer either to the MOF or the analyte, or the combination of the two.

Example 1

A SAW device can be provided including a thin film of the MOF HKUST-1 infiltrated with TCNQ deposited on the surface of the SAW, covering the entire surface, including the electrodes. A phase and amplitude detection method (e.g., see U.S. Pat. No. 5,763,283 of Cernosek, et al.) can be used to detect a presence of an analyte.

A device as described would measure simultaneously: (1) a phase and amplitude of an acoustic wave propagating horizontal to the surface of the SAW (the standard SAW detection mode) and (2) an electrical conductivity of the nanoporous MOF+TCNQ film. Molecules adsorbed within the MOF pores would alter the phase of the acoustic wave and change the film conductivity, providing two simultaneous, independent responses to the presence of analyte molecules.

Example 2

Figure 3:
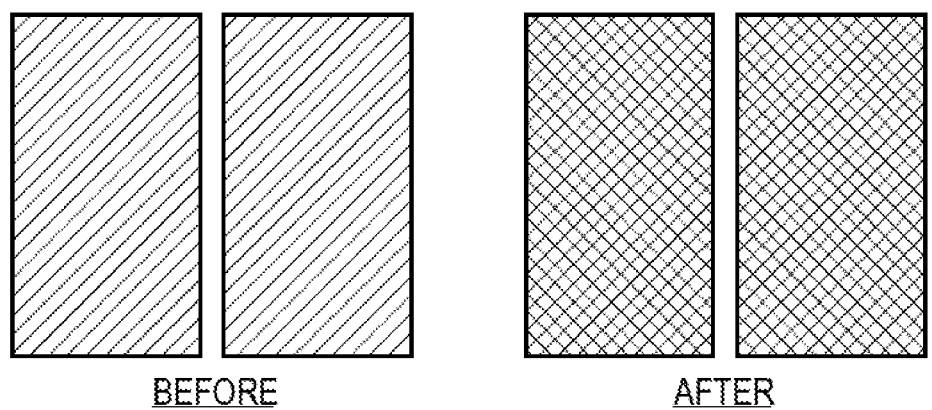
FIG. 3 shows a sensing device including a film of HKUST-1 MOF deposited on rectangular gold electrodes before and after infiltration with 7,7,8,8-tetracyanoquinododimethane (TCNQ).
Figure 4:
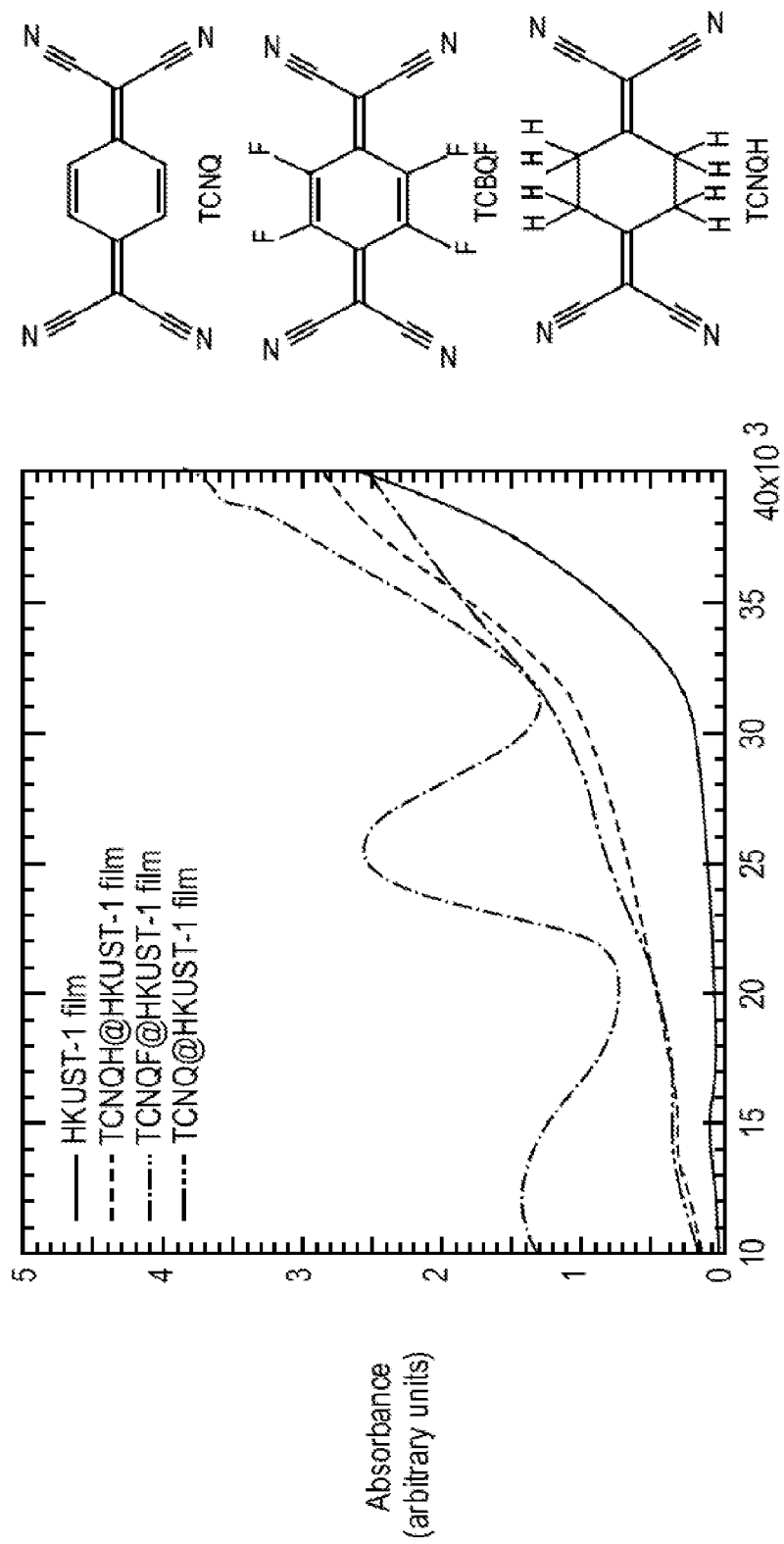
FIG. 4 shows absorption spectra of the MOF film of FIG. 3 before and after infiltration with TCNQ.

FIG. 3 shows a sensing device comprised of a film of the MOF HKUST-1 (the structure of which is shown in the inset) deposited on rectangular gold electrodes deposited, for example, on an oxidized surface of a material such as a semiconductor material (e.g., silicon). The film covers the entire device. "Before" picture shows the color of the film before the molecule TCNQ is detected by filling the pores; the absorption spectrum of this film prior to detecting TCNQ is shown in FIG. 4 as the solid trace. The "After" image shows the same device in the presence of TCNQ. A measurable change in color occurs as schematically illustrated in FIG. 3 and as seen in the absorption spectrum in FIG. 4 (dash dot trace). The interaction of the device with TCNQ can also be detected by measuring the reflectance of the device. FIG. 4 also shows the absorption spectra of HKUST-1 films infiltrated with cyclohexane-(1,4-diylidene)dimalononitrile (TCNQH; dash dash trace) and 2,3,5,6-tetrafluoro-7,7,8,8-tetracyanoquinodimethane (TCNQF; dash dot dot trace), species related to TCNQ.

Figure 5:
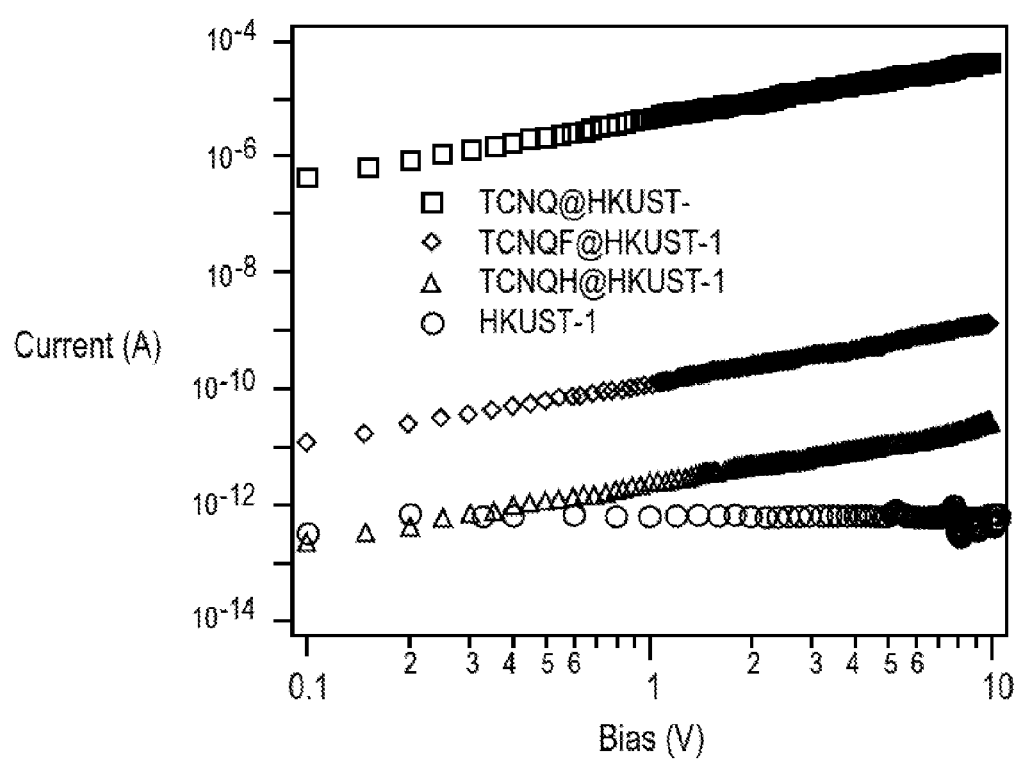
FIG. 5 shows plots of electrical conductivity as a function of applied bias for an HKUST-1 film before and after infiltration with TCNQ.

Simultaneous with a change in the absorbance or reflectivity of the device, the electrical conductivity of the device changes dramatically. As seen in FIG. 5, prior to exposure to TCNQ (HKUST-1 line), the electrical conductivity as a function of applied bias is extremely low. Upon exposure to TCNQ (green squares), the electrical conductivity increases by over six orders of magnitude. The color of the film, as measured by the intensity of the absorption bands in FIG. 4, will change linearly with TCNQ loading (photon absorbance is linear with the concentration of the absorbing species for constant film thickness). In contrast, the electronic conductivity exhibits a square-root dependence on concentration of TCNQ in the pores because the formation of conducting chains of TCNQ molecules bound to the HKUST-1 film follows a percolation model. FIG. 5 also shows the electrical conductivity of HKUST-1 films infiltrated with cyclohexane-(1,4-diylidene)dimalononitrile (TCNQH; triangles) and 2,3,5,6-tetrafluoro-7,7,8,8-tetracyanoquinodimethane (TCNQF; diamonds), species related to TCNQ to indicate conductivity shifts with these other species.

The combined measurements of absorbance (or reflectivity) and electrical conductivity, which exhibit different dependencies on the amount of TCNQ analyte interacting with the device demonstrates the concept of multi-axis sensing. In addition, the changes in color and electrical conductivity for TCNQ are very different from those caused by the TCNQH and TCNQF, demonstrating that multi-axis sensing can distinguish an analyte from other chemically similar structures.

In the description above, for the purposes of explanation, numerous specific details have been set forth in order to provide a thorough understanding of the embodiments. It will be apparent however, to one skilled in the art, that one or more other embodiments may be practiced without some of these specific details. The particular embodiments described are not provided to limit the invention but to illustrate it. The scope of the invention is not to be determined by the specific examples provided above but only by the claims below. In other instances, well-known structures, devices, and operations have been shown in block diagram form or without detail in order to avoid obscuring the understanding of the description. Where considered appropriate, reference numerals or terminal portions of reference numerals have been repeated in the figure to indicate corresponding or analogous elements, which may optionally have similar characteristics.

It should also be appreciated that reference throughout this specification to "one embodiment", "an embodiment", "one or more embodiments", or "different embodiments", for example, means that a particular feature may be included in the practice of the invention. Similarly, it should be appreciated that in the description, various features are sometimes grouped together in a single embodiment, figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in less than all features of a single disclosed embodiment. Thus, the claims following the Detailed Description are hereby expressly incorporated into this Detailed Description, with each claim standing on its own as a separate embodiment of the invention.

What is claimed is:

1. A sensor device comprising:
a sensor substrate; and
a thin film comprising a porous organic metal framework (MOF) on the sensor substrate that is configured to present more than one transduction mechanism when exposed to an analyte, which thereby enables multi-axis sensing.

2. The sensor device of claim 1, wherein the more than one transduction mechanism comprises more than one of electrical conductivity, strain, acoustic modification, optical absorption or optical emission.

3. The sensor device of claim 1, wherein the device comprises a surface acoustic wave sensor device and the sensor substrate is a piezoelectric substrate.

4. The sensor device of claim 3, wherein a first of the more than one transduction mechanism is an acoustic modification and a second of the more than one transduction mechanism is optical absorption.

5. The sensor device of claim 1, wherein the sensor substrate is a cantilever beam.

6. The sensor device of claim 5, wherein one of the more than one transduction mechanism is strain on a material of the cantilever beam.

7. The sensor device of claim 6, wherein one of the more than one transduction mechanism is optical absorption.

8. The sensor device of claim 1, wherein one of the more than one transduction mechanism is a change in an electrical property.

9. The sensor device of claim 1, wherein the MOF is modified with a guest species.

10. A method comprising:
exposing a porous metal organic framework (MOF) on a substrate to an analyte; and
identifying more than one transduction mechanism in response to the exposure to the analyte, thereby enabling multi-axis sensing.

11. The method of claim 10, wherein the more than one transduction mechanism comprises more than one of electrical conductivity, strain, acoustic modification, optical absorption or optical emission.

12. The method of claim 10, wherein the substrate is a piezoelectric substrate of a surface acoustic wave sensor.

13. The method of claim 12, wherein a first of the more than one transduction mechanism is an acoustic modification and a second of the more than one transduction mechanism is optical absorption.

14. The method of claim 10, wherein the substrate is a cantilever beam.

15. The method of claim 14, wherein one of the more than one transduction mechanism is strain on a material of the cantilever beam.

16. The method of claim 10, wherein one of the more than one transduction mechanism is optical absorption.

17. The method of claim 10, wherein one of the more than one transduction mechanism is a change in an electrical property.

18. The method of claim 10, wherein the MOF is modified with a guest species.

* * * * *